(12) United States Patent
Hu et al.

(10) Patent No.: US 9,498,394 B2
(45) Date of Patent: Nov. 22, 2016

(54) ABSORBENT PAD, ABSORBENT ARTICLE, AND METHOD FOR MANUFACTURING AN ABSORBENT PAD

(71) Applicant: Kang Na Hsiung Enterprise Co., Ltd., Tainan (TW)

(72) Inventors: Yen-Jung Hu, Tainan (TW); Chih-Hsiang Lin, Tainan (TW)

(73) Assignee: KANG NA HSIUNG ENTERPRISE CO., LTD., Tainan (TW)

( * ) Notice: Subject to any disclaimer, the term of this patent is extended or adjusted under 35 U.S.C. 154(b) by 170 days.

(21) Appl. No.: 14/089,676

(22) Filed: Nov. 25, 2013

(65) Prior Publication Data

US 2014/0148772 A1    May 29, 2014

(30) Foreign Application Priority Data

Nov. 28, 2012   (TW) ............................. 101144479 A

(51) Int. Cl.
| | | |
|---|---|---|
| *A61F 13/42* | (2006.01) | |
| *A61F 13/49* | (2006.01) | |
| *A61F 13/15* | (2006.01) | |
| *A61F 13/84* | (2006.01) | |

(52) U.S. Cl.
CPC ... *A61F 13/49058* (2013.01); *A61F 13/15699* (2013.01); *A61F 13/42* (2013.01); *A61F 2013/424* (2013.01); *A61F 2013/8479* (2013.01)

(58) Field of Classification Search
CPC .. A61F 13/42; A61F 13/44; A61F 2013/424; A61F 2013/8476; A61F 2013/8479; A61F 2013/8482

USPC .......................................................... 604/362
See application file for complete search history.

(56) References Cited

U.S. PATENT DOCUMENTS

| | | | | |
|---|---|---|---|---|
| 4,356,818 A | * | 11/1982 | Macias .................. | A61F 13/42 128/886 |
| 5,760,694 A | * | 6/1998 | Nissim .................... | A61F 13/42 128/885 |
| 8,196,809 B2 | * | 6/2012 | Thorstensson .......... | A61F 13/42 235/375 |
| 8,978,452 B2 | * | 3/2015 | Johnson ............... | G01N 27/223 340/604 |
| 2002/0021220 A1 | * | 2/2002 | Dreyer ................... | A47K 11/04 340/573.1 |
| 2003/0020615 A1 | * | 1/2003 | Zand ....................... | A61F 13/42 340/573.5 |
| 2005/0156744 A1 | * | 7/2005 | Pires ....................... | A61F 13/42 340/573.5 |
| 2011/0095884 A1 | * | 4/2011 | Xu ........................... | A61F 13/42 340/539.11 |

* cited by examiner

*Primary Examiner* — Lynne Anderson
(74) *Attorney, Agent, or Firm* — DLA Piper LLP (US)

(57) ABSTRACT

An absorbent article for use with a RF reader includes an absorbent pad and a RFID tag. The absorbent pad includes a lining layer, a liquid-impermeable layer, an absorbent layer, and a plurality of sensing wires. The liquid-impermeable layer is attached to the lining layer. The absorbent layer is disposed between the lining layer and the liquid-impermeable layer. The lining layer and the liquid-impermeable layer define a receiving space having an opening located at a side portion of the absorbent pad. The sensing wires are provided on the absorbent layer and extend into the receiving space. The RFID tag is received in the receiving space and contacts electrically the sensing wires when received in the receiving space.

16 Claims, 9 Drawing Sheets ated Taiwanese Application
ABSORBENT PAD, ABSORBENT ARTICLE, AND METHOD FOR MANUFACTURING AN ABSORBENT PAD

CROSS-REFERENCE TO RELATED APPLICATION

This application claims priority of Taiwanese Application No. 101144479, filed on Nov. 28, 2012.

BACKGROUND OF THE INVENTION

1. Field of the Invention

The invention relates to an absorbent article, more particularly to an absorbent article that is capable of sensing wetness thereof.

2. Description of the Related Art

As shown in FIG. 1, a conventional diaper 1, which is capable of indicating if it is wet, comprises an outer liquid-impermeable layer 11, an inner lining layer 12, an absorbent layer 13 that is disposed between the outer impermeable-layer 11 and the inner lining layer 12, and a sensing conductor set 14 in contact with the absorbent layer 13. The outer liquid-impermeable layer 11 is provided with a pocket 111 on an outer surface thereof for receiving a signal transmitter 15. The sensing conductor set 14 includes three spaced-apart sensing wires 141 each of which has one end extending to penetrate through the outer liquid-impermeable layer 11 and into the pocket 111 for electrically coupling to the signal transmitter 15.

When the conventional diaper 1 is in use and the absorbent layer 13 absorbs liquid or moisture from human waste (such as urine or the like), the sensing wires 141 of the sensing conductor set 14 cooperatively form an electrical loop due to wetness of the absorbent layer 13 and enable the signal transmitter 15 to transmit a signal to a signal receiver (not shown) for generating an indicating signal, in the form of light or sound, to inform a caregiver that the conventional diaper 1 needs to be changed.

However, when manufacturing the conventional diaper 1, an additional manufacturing step is needed for forming the pocket 111 on the outer surface of the outer liquid-impermeable layer 11, thereby increasing the manufacturing complexity and cost due to material consumption. Moreover, since the sensing conductor set 14 needs to be disposed between the outer liquid-impermeable layer 11 and the inner lining layer 12, steps of cutting and assembling the sensing conductor set 14 need to be performed before assembling the sensing conductor set 14 with other components of the conventional diaper 1. Furthermore, the sensing wires 141 of the sensing conductor set 14 extend to penetrate through the outer liquid-impermeable layer 11 and into the pocket 141 to contact electrically with the signal transmitter 15, such that liquid may leak outwardly from the liquid-impermeable layer 11 via holes through which the sensing wires 141 extend.

SUMMARY OF THE INVENTION

Therefore, the object of the present invention is to provide an absorbent article that may alleviate the aforementioned drawbacks of the prior art.

According to one aspect of the present invention, an absorbent pad comprises a lining layer, a liquid-impermeable layer, an absorbent layer, and a plurality of sensing wires. The liquid-impermeable layer is attached to the lining layer. The absorbent layer is disposed between the lining layer and the liquid-impermeable layer. The lining layer and the liquid-impermeable layer cooperate to define a receiving space that has an opening located at a side portion of the absorbent pad. The sensing wires are provided on the absorbent layer and extend into the receiving space.

According to another aspect of the present invention, an absorbent article is adapted to use with a RF reader and comprises the abovementioned absorbent pad and a radio-frequency identification (RFID) tag. The RFID tag is removably received in the receiving space through the opening and contacts electrically the sensing wires when received in the receiving space.

According to yet another aspect of the present invention, a method for manufacturing an absorbent pad comprises the steps of:

placing an absorbent layer on a liquid-impermeable material, the absorbent layer having an area smaller than that of the liquid-impermeable material;

applying an adhesive on the absorbent layer and the liquid-impermeable material;

providing a plurality of sensing wires on the absorbent layer, each of the sensing wires having a connection portion that extends beyond a periphery of the absorbent layer;

providing a release paper on the connection portions of the sensing wires;

applying an adhesive on one side of the release paper opposite to the liquid-impermeable material;

adhering a lining material onto the liquid-impermeable material, the absorbent layer and the release paper, the lining material covering the absorbent layer and the release paper and being prevented by the release paper from adhering to the liquid-impermeable material at a vicinity of the connection portions of the sensing wires; and cutting the lining material, the liquid-impermeable material and the sensing wires to form the absorbent pad, wherein one side portion of the absorbent pad is adjacent to the release paper and is formed with an opening into a receiving space that is cooperatively defined by the lining material and the liquid-impermeable material and that receives the connection portions of the sensing wires.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
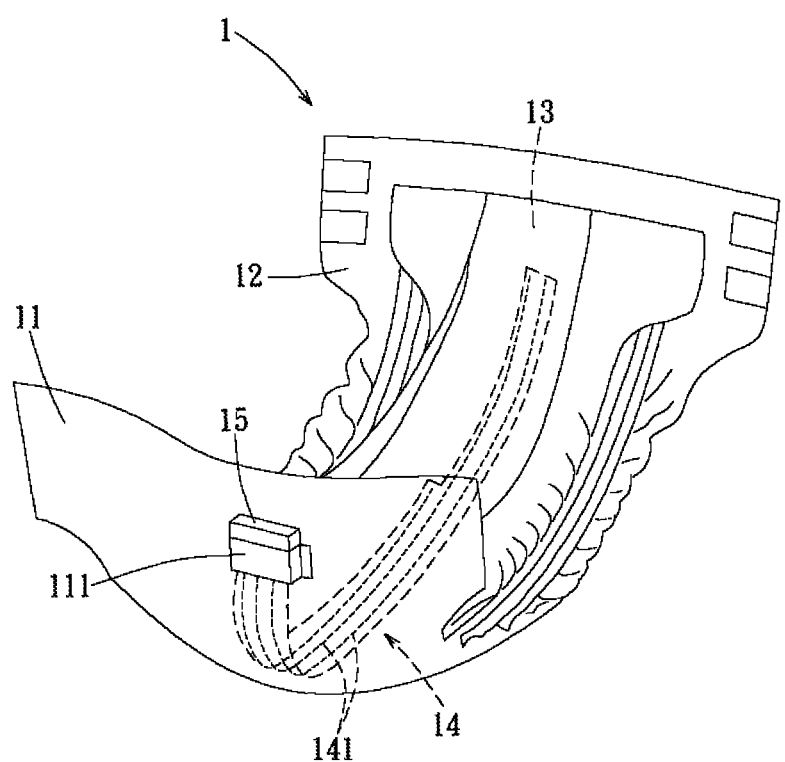
FIG. 1 is a perspective view of a conventional absorbent article.
Figure 2:
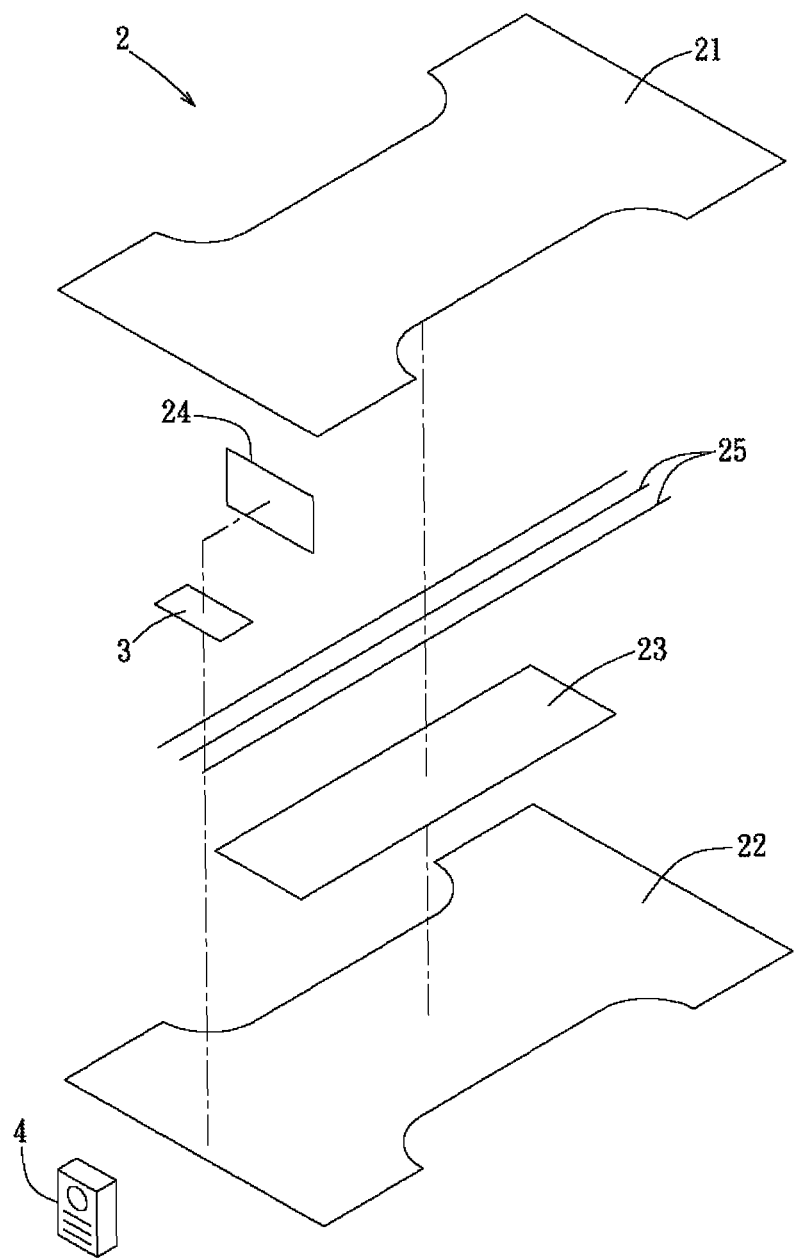
FIG. 2 is an exploded perspective view showing a first preferred embodiment of an absorbent article, together with a RF reader, according to the present invention.
Figure 3:
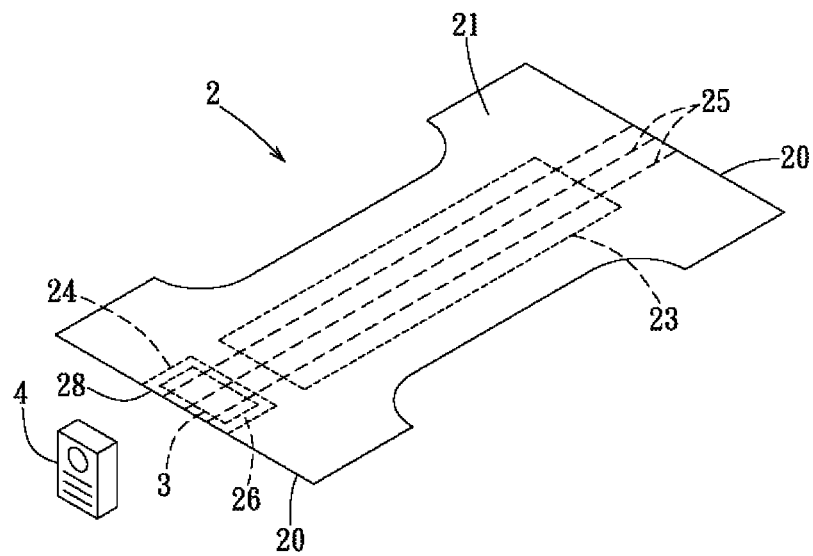
FIG. 3 is an assembled perspective view of the first preferred embodiment together with the RF reader.
Figure 4:
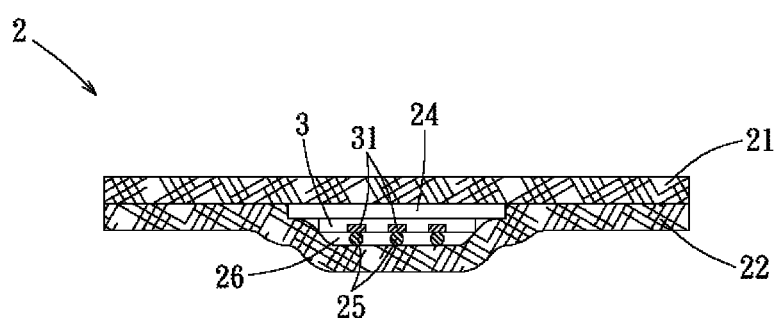
FIG. 4 is a side view of the first preferred embodiment.

Before the present invention is described in greater detail, it should be noted that like elements are denoted by the same reference numerals throughout the disclosure.

As shown in FIGS. 1 to 4, the first preferred embodiment of an absorbent article according to the present invention is exemplified as a diaper that is adapted for use with a RF reader 4 and that comprises an absorbent pad 2 and a RFID tag 3.

The absorbent pad 2 includes a lining layer 21, a liquid-impermeable layer 22, an absorbent layer 23, and a plurality or sensing wires 25. In this embodiment, the absorbent pad 2 has a pair of first and second side portions 20 opposite to each other.

In this embodiment, the lining layer 21 contains at least one of an anti-bacterial agent and a far-infrared radiation powder. The anti-bacterial agent and the far-infrared radiation powder may be added to the lining layer 21 by spraying, coating, printing, or other equivalent methods.

The liquid-impermeable layer 22 is attached to the lining layer 21.

The absorbent layer 23 is disposed between the lining layer 21 and the liquid-impermeable layer 22 and is spaced apart from the first and second side portions 20. Preferably, the absorbent layer 23 is configured to have an area smaller than that of the absorbent pad 2, and a periphery of the absorbent layer 23 is spaced apart from a periphery of the absorbent pad 2. The lining layer 21 and the liquid-impermeable layer 22 cooperate to define a first receiving space 26 that has a first opening 28 located at the first side portion 20 of the absorbent pad 2. The first receiving space 26 is isolated from the absorbent layer 23 by an adhesive seam between the lining layer 21 and the liquid-impermeable layer 22.

The sensing wires 25 are provided on the absorbent layer 23 and extend into the first receiving space 26. In this embodiment, there are three spaced-apart sensing wires 25 provided in the absorbent pad 2, but the number of the sensing wires 25 is not limited so long as at least two sensing wires 25 are adopted in the absorbent pad 2. Each of the sensing wires 25 is provided between the absorbent layer 23 and one of the lining layer 21 and the liquid-impermeable layer 22. In this embodiment, the sensing wires 25 are provided between the absorbent layer 23 and the lining layer 21 to achieve better sensitivity thereof. Preferably, each of the sensing wires 25 is made of a metallic material and has an outer diameter that is smaller than 0.1 mm. Such small size of the sensing wires 25 does not cause discomfort to a wearer.

The RFID tag 3 is removably received in the first receiving space 26 through the first opening 23 and contacts electrically the sensing wires 25 when received in the first receiving space 26.

Preferably, one of the lining layer 21 and the liquid-impermeable layer 22 is provided with an adhesive (not shown) to removably retain the RFID tag 3 in the first receiving space 26. In this embodiment, the liquid-impermeable layer 22 is provided with the adhesive. Moreover, the absorbent article preferably further comprises a release paper 24 that is disposed between the lining layer 21 and the liquid-impermeable layer 22 and that prevents the lining layer 21 and the liquid-impermeable layer 22 from adhering to each other at the first receiving space 26.

In this embodiment, the RFID tag 3 is disposed between the release paper 24 and the sensing wires 25 when received in the receiving space 26. The RFID tag 3 has a plurality of contact points 31 each of which is in electrical contact with a respective one of the sensing wires 25 when received in the first receiving space 26. Since the liquid-impermeable layer 22 is provided with the adhesive, there is no need to provide additional clips or connectors to establish electrical connection between the RFID tag 3 and the sensing wires 25. In addition, undesired movement of the RFID tag 3 in the first receiving space 26 may be avoided to ensure stable electrical connection. The size of the RFID tag 3 may be reduced to minimize discomfort of the wearer attributed to the RFID tag 3. Moreover, since the RFID tag 3 is a passive electronic component that does not need batteries to provide electrical power thereto, the size of the RFID tag 3 is relatively small. However, the RFID tag 3 may be an active electrical component in other embodiments of the present invention. Further, since the RFID tag 3 is removably received in the first receiving space 26 of the absorbent pad 2, the RFID tag 3 is reusable and can be applied to another replacement absorbent pad 2.

When the absorbent layer 23 absorbs liquid or moisture from human waste, the sensing wires 25 cooperate with the RFID tag 3 to form a circuit due to wetness of the absorbent layer 23. The circuit has electrical characteristics (such as resistance) that change with amount of liquid absorbed by the absorbent layer 23, such that various types or various amount of human waste may be detected. The RF reader 4 is configured to communicate with the RFID tag 3 for detecting the wetness of the absorbent layer 23 and to generate an indicating signal to indicate to a caregiver that the absorbent pad 2 is wet, so as to allow the caregiver to make a timely response. Moreover, in this embodiment, the RFID tag 3 communicates with the RF reader 4 in a wireless manner, so the RF reader 4 does not require physical contact with the wearer and can be disposed beside the absorbent pad 2 or carried portably by the caregiver. Furthermore, the RF reader 4 may generate different indicating signals corresponding to different levels of wetness of the absorbent layer 23. The indicating signals may be in the form of light, sound, vibration and the like, and may be wireless transmitted signals to an external managing device (such as a computer of a nursing station, a cellular phone, etc.) for managing a plurality of the absorbent articles to perform systematic detection (or analysis).

Figure 5:
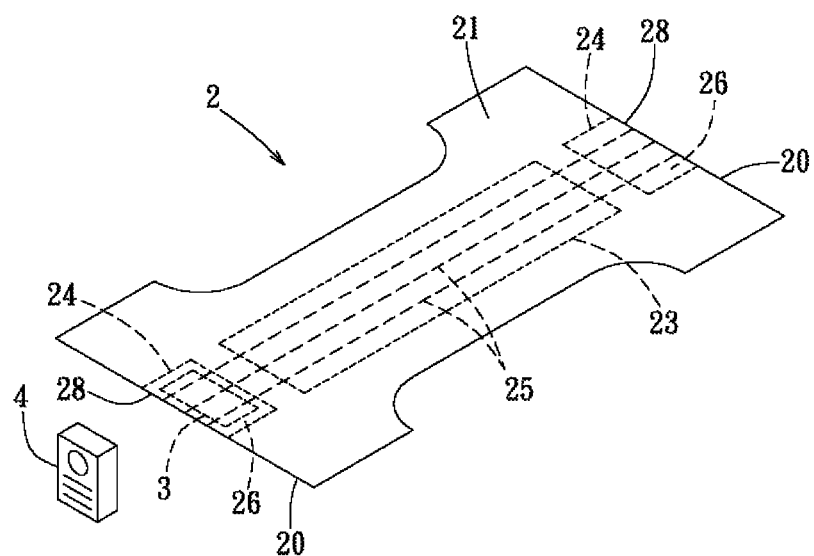
FIG. 5 is a perspective view showing a second preferred embodiment of the absorbent article, together with the RF reader, according to the present invention.

Referring to FIG. 5, a second preferred embodiment of the absorbent article according to the present invention is shown to be similar to that of the first preferred embodiment. The difference therebetween resides in that the lining layer 21 and the liquid-impermeable layer 22 of the second preferred embodiment further cooperate to define a second receiving space 26 that has a second opening 28 located at the second side portion 20 of the absorbent pad 2 for receiving the RFID tag 3. The sensing wires 25 further extend into the second receiving space 26, and the RFID tag 3 is removably received in the second receiving space 26 through the second opening 28 and contacts electrically the sensing wires 25 when received in the second receiving space 26. Preferably, one of the lining layer 21 and the liquid-impermeable layer 22 is provided with an adhesive to removably retain the RFID tag 3 in the second receiving space 26. In this embodiment, the absorbent article further comprises a second release paper 24 that is disposed in the second receiving space 26 and that prevents the lining layer 21 and the liquid-impermeable layer 22 from adhering to each other in the second receiving space 26. By such design, the location of the RFID tag 3 can be adjusted according to user's demand. For example, when the wearer lies on his/her back (corresponding to one of the first and second receiving spaces 26), the location of the RFID tag 3 can be adjusted to the belly side (i.e., corresponding to the other one of the first and second receiving spaces 26), so as to assure the comfort of the wearer.

Figure 6:
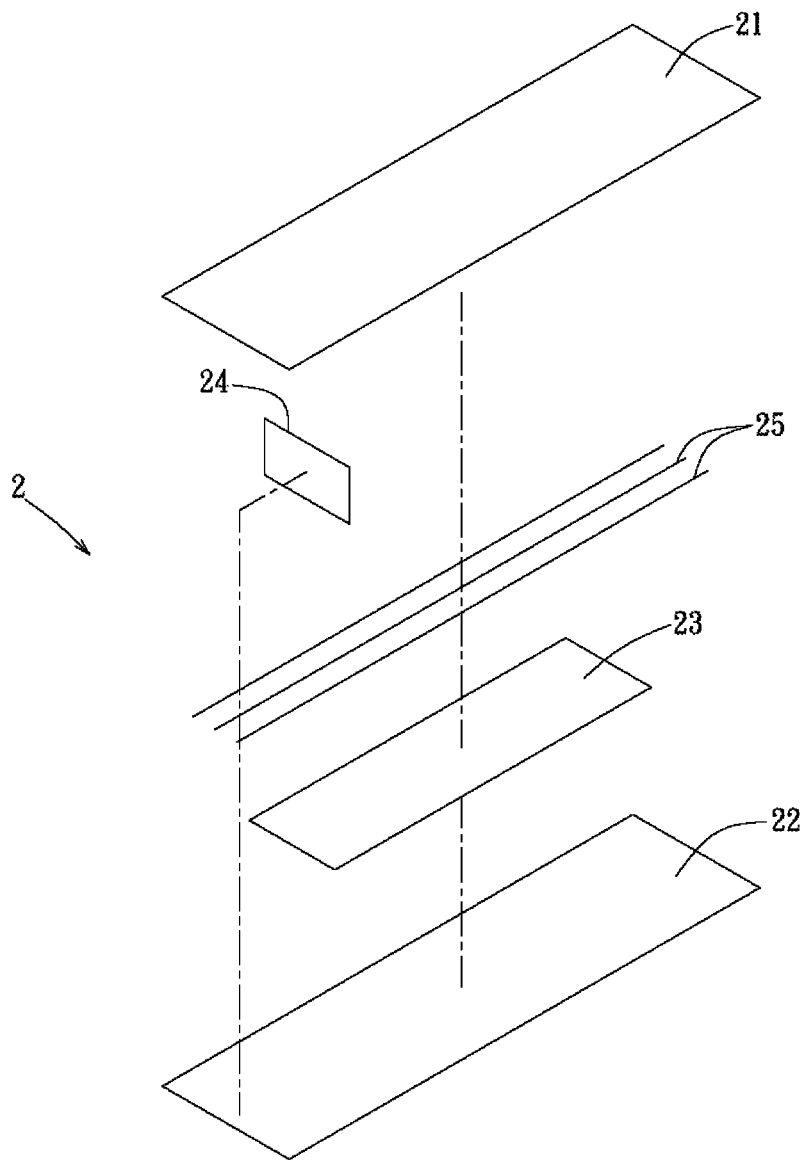
FIG. 6 is an exploded perspective view of a third preferred embodiment of an absorbent pad according to the present invention.
Figure 7:
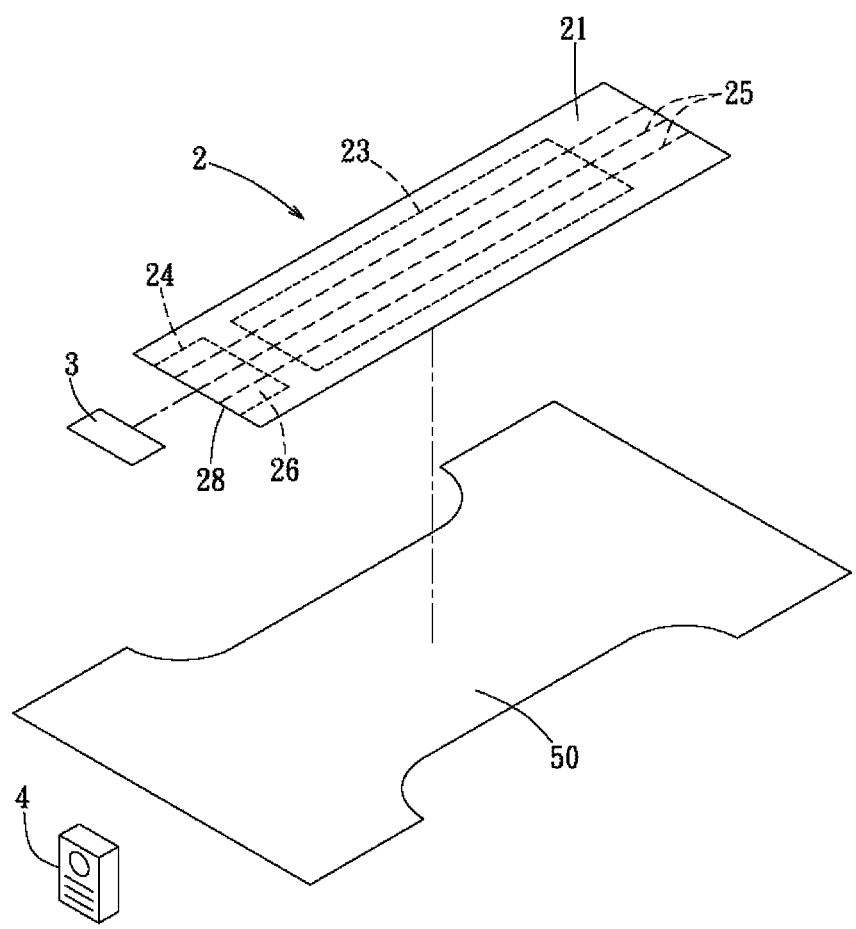
FIG. 7 is a perspective view showing the absorbent pad and an undergarment of the third preferred embodiment, together with the RF reader.
Figure 8:
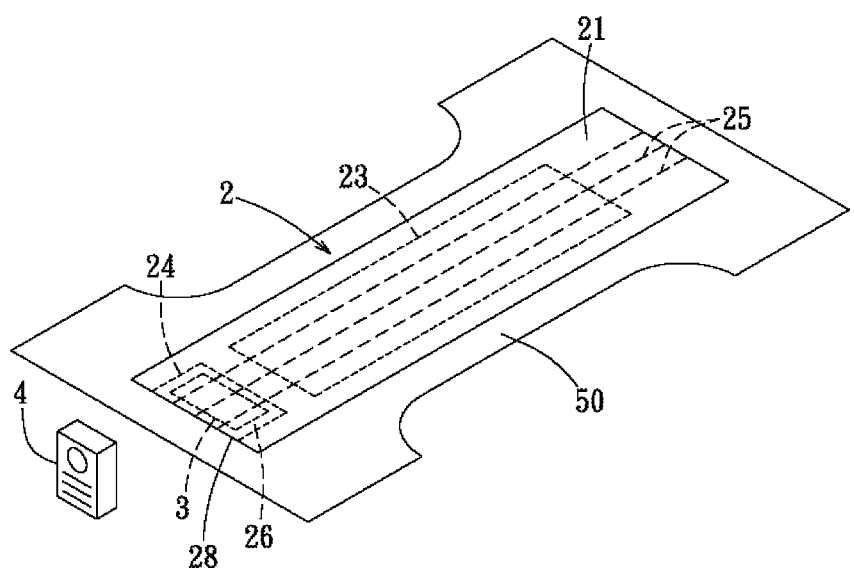
FIG. 8 is a perspective view of the third preferred embodiment.
Figure 9:
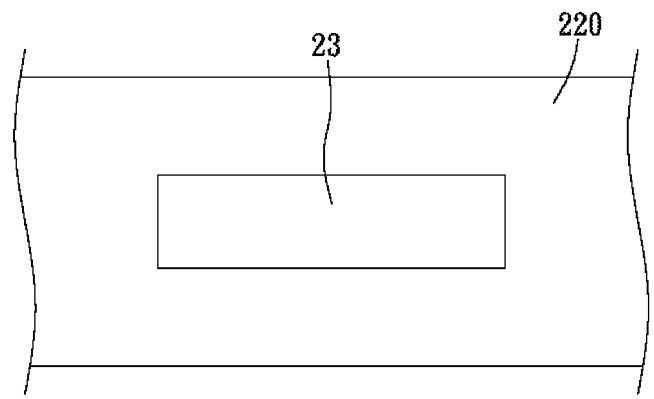
FIGS. 9 to 12 illustrate the preferred embodiment of a method for manufacturing the absorbent pad according to the present invention.

Referring to FIGS. 6 to 8, a third preferred embodiment of the absorbent article is shown to be similar to that of the first preferred embodiment. In this embodiment, the absorbent article further comprises an undergarment 50 that is to serve as a diaper. In this embodiment, the absorbent pad 2 is configured in a substantially rectangular shape smaller than an area of the undergarment 50 and is removably attached to the undergarment 50. While using the absorbent article of the third preferred embodiment, the RFID tag 3 is first received in the first receiving space 26 of the absorbent pad 2, and then the absorbent pad 2 is placed on the undergarment 50, followed by putting the undergarment 50 on the wearer. Owing to the liquid-impermeable layer 22, human waste will not permeate to reach the undergarment 50. Thus, only the absorbent pad 2 needs to be replaced when the absorbent pad 2 is wet, so as to result in lower manufacturing costs.

Referring to FIGS. 9 to 12, a method for manufacturing the absorbent pad of the first preferred embodiment is shown to include the following steps.

Step 1: placing an absorbent layer 23 on a liquid-impermeable material 220. The absorbent layer 23 has an area smaller than that of the liquid-impermeable material 220 (see FIG. 9).

Step 2: applying an adhesive on the absorbent layer 23 and the liquid-impermeable material 220.

Figure 10:
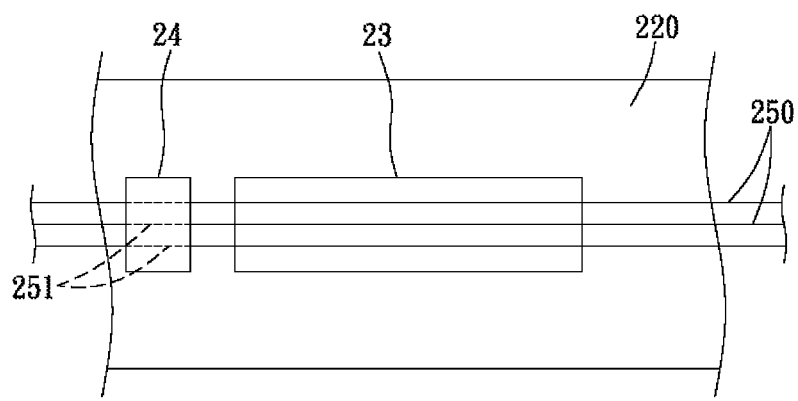

Step 3: providing a plurality of sensing wires 250 on the absorbent layer 23 (see FIG. 10). Each of the sensing wires 250 has a connection portion 251 that extends beyond a periphery of the absorbent layer 23. In this embodiment, the sensing wires 250 are under tension when provided on the absorbent layer 23 and are arranged to extend parallel to each other.

Step 4: providing a release paper 24 on the connection portions 251 of the sensing wires (see FIG. 10). The release paper 24 is spaced apart from the absorbent layer 23.

Step 5: applying an adhesive on one side of the release paper 24 opposite to the liquid-impermeable material 220.

Figure 11:
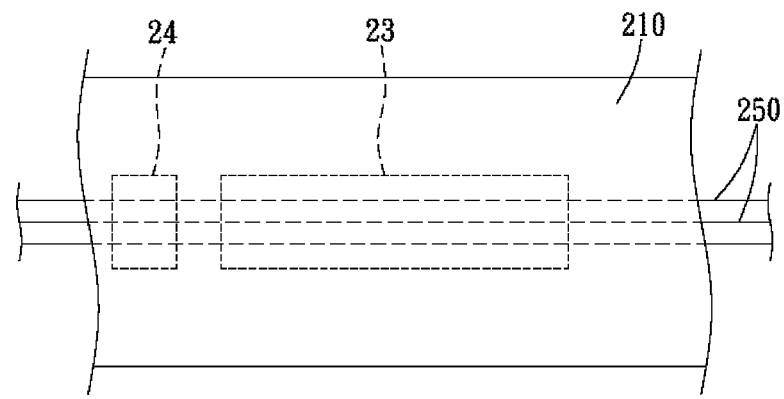

Step 6: adhering a lining material 210 onto the liquid-impermeable material 220, the absorbent layer 23, and the release paper 24 (see FIG. 11). The lining material 210 covers the absorbent layer 23 and the release paper 24 and is prevented by the release paper 24 from adhering to the liquid-impermeable material 220 at a vicinity of the connection portions 251 of the sensing wires 25.

Figure 12:
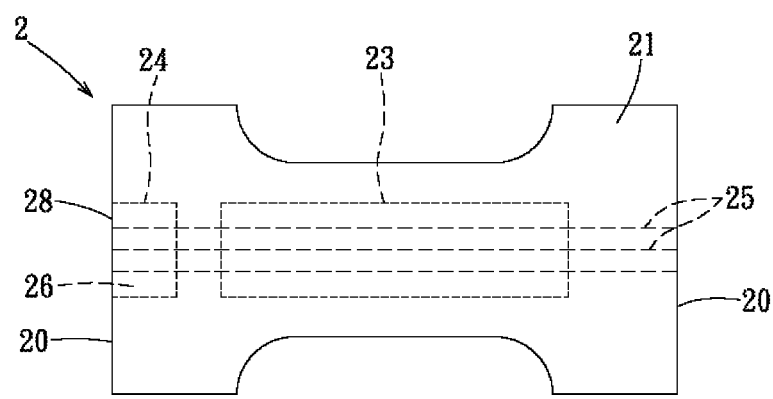

Step 7: cutting the lining material 210, the liquid-impermeable material 220, and the sensing wires 25 to form the absorbent pad 2 of the first preferred embodiment (see FIG. 12). One side portion 20 of the absorbent pad 2 is adjacent to the release paper 24 and is formed with an opening 23 into a first receiving space 26 that is cooperatively defined by the lining material 210 and the liquid-impermeable material 220 and that receives the connection portions 251 of the sensing wires 25.

By utilizing the release paper 24, the lining layer 21 and the liquid-impermeable layer 22 are prevented from adhering to each other, so as to allow the first receiving space 26 to be defined thereby cooperatively. Thus, there is no need to perform an additional process to provide a pocket on an outer surface of the liquid-impermeable layer 22 for receiving the RFID tag 3, so as to lower the manufacturing complexity and cost. Moreover, the sensing wires 250 are simultaneously cut with the lining material 210 and the liquid-impermeable material 220, so that additional processes to cut the sensing wires 250 into segments with appropriate length and to assemble the sensing wire segments with other components in the absorbent article are not needed in the method of this invention. Furthermore, the release paper 24 is removably adhered to the liquid-impermeable layer 22 and the RFID tag 3 can be adhered removably to the liquid-impermeable layer 22. Even further, the first receiving space 26 is cooperatively defined by the lining layer 21 and the liquid-impermeable layer 22, and the sensing wires 25 do not need to penetrate through the liquid-impermeable layer 22, thereby preventing leakage through the absorbent pad 2.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. An absorbent article adapted for use with a radio frequency reader, said absorbent article comprising:
   an absorbent pad including
   a lining layer,
   a liquid-impermeable layer attached to said lining layer,
   an absorbent layer disposed between said lining layer and said liquid-impermeable layer,
   said lining layer and said liquid-impermeable layer cooperating to define a first receiving space that has a first opening located at a first side portion of said absorbent pad, and
   a plurality of sensing wires provided on said absorbent layer and extending into said first receiving space; and
   a radio-frequency identification (RFID) tag removably received in said first receiving space through said first opening and contacting electrically said sensing wires when received in said first receiving space,
   wherein said absorbent pad further includes
   an adhesive that adheres said lining layer to said liquid-impermeable layer, and that has a portion in said first receiving space to removably retain said RFID tag therein, and
   a release paper that is disposed between said portion of said adhesive and one of said lining layer and said liquid-impermeable layer, and that prevents said lining layer and said liquid-impermeable layer from adhering to each other at said first receiving space.

2. The absorbent article as claimed in claim 1, wherein said RFID tag is disposed between said release paper and said sensing wires when received in said first receiving space.

3. The absorbent article as claimed in claim 1, wherein said absorbent layer is configured to have an area smaller than that of said absorbent pad, and a periphery of said absorbent layer is spaced apart from a periphery of said absorbent pad.

4. The absorbent article as claimed in claim 1, wherein each of said sensing wires is provided between said absorbent layer and one of said lining layer and said liquid-impermeable layer.

5. The absorbent article as claimed in claim 1, wherein each of said sensing wires is made of a metallic material and has an outer diameter that is smaller than 0.1 mm.

6. The absorbent article as claimed in claim 1, wherein:
said lining layer and said liquid-impermeable layer further cooperate to define a second receiving space that has a second opening located at a second side portion of said absorbent pad, said second side portion being opposite to said first side portion;
said sensing wires further extend into said second receiving space; and
said RFID tag is removably received in said second receiving space through said second opening and contacts electrically said sensing wires when received in said second receiving space.

7. The absorbent article as claimed in claim 1, wherein said lining layer contains at least one of an antibacterial agent and a far-infrared radiation powder.

8. The absorbent article as claimed in claim 1, wherein said RFID tag cooperates with said sensing wires to form a circuit having electrical characteristics that change with amount of liquid absorbed by said absorbent layer,
whereby the radio frequency reader is configured to communicate with said RFID tag for detecting wetness of said absorbent layer.

9. The absorbent pad as claimed in claim 8, wherein said absorbent layer is configured to have an area smaller than that of said absorbent pad, and a periphery of said absorbent layer is spaced apart from a periphery of said absorbent pad.

10. The absorbent pad as claimed in claim 8, wherein each of said sensing wires is provided between said absorbent layer and one of said lining layer and said liquid-impermeable layer.

11. The absorbent pad as claimed in claim 8, wherein each of said sensing wires is made of a metallic material and has an outer diameter that is smaller than 0.1 mm.

12. The absorbent pad as claimed in claim 8, wherein:
said lining layer and said liquid-impermeable layer further cooperate to define a second receiving space that has a second opening located at a second side portion of said absorbent pad, said second side portion being opposite to said first side portion; and
said sensing wires further extend into said second receiving space.

13. The absorbent pad as claimed in claim 8, wherein said lining layer contains at least one of an antibacterial agent and a far-infrared radiation powder.

14. An absorbent pad comprising:
a lining layer;
a liquid-impermeable layer attached to said lining layer;
an absorbent layer disposed between said lining layer and said liquid-impermeable layer;
said lining layer and said liquid-impermeable layer cooperating to define a first receiving space that has a first opening located at a first side portion of said absorbent pad; and
a plurality of sensing wires provided on said absorbent layer and extending into said first receiving space,
wherein said absorbent pad further includes:
an adhesive layer that adheres said lining layer to said liquid-impermeable layer, and that has a portion extending into said first receiving space to removably retain said RFID tag therein; and
a release paper that is disposed between said portion of said adhesive and one of said lining layer and said liquid-impermeable layer, and that prevents said lining layer and said liquid-impermeable layer from adhering to each other at said first receiving space.

15. A method for manufacturing an absorbent pad, comprising the steps of:
placing an absorbent layer on a liquid-impermeable material, the absorbent layer having an area smaller than that of the liquid-impermeable material;
applying an adhesive on the absorbent layer and the liquid-impermeable layer;
providing a plurality of sensing wires on the absorbent layer, each of the sensing wires having a connection portion that extends beyond a periphery of the absorbent layer;
providing a release paper on the connection portions of the sensing wires;
applying an adhesive on one side of the release paper opposite to the liquid-impermeable material;
adhering a lining material onto the liquid-impermeable material, the absorbent layer and the release paper, the lining material covering the absorbent layer and the release paper and being prevented by the release paper from adhering to the liquid-impermeable material at a vicinity of the connection portions of the sensing wires; and
cutting the lining material, the liquid-impermeable material and the sensing wires to form the absorbent pad, wherein one side portion of the absorbent pad is adjacent to the release paper and is formed with an opening into a receiving space that is cooperatively defined by the lining material and the liquid-impermeable material and that receives the connection portions of the sensing wires.

16. The method as claimed in claim 15, wherein the sensing wires are under tension when provided on the absorbent layer and are arranged to extend parallel to each other.

* * * * *